United States Patent
Basinger et al.

(10) Patent No.: US 10,111,776 B2
(45) Date of Patent: Oct. 30, 2018

(54) IMPLANTABLE INTRAOCULAR DRUG DELIVERY APPARATUS, SYSTEM AND METHOD

(71) Applicant: ABBOTT MEDICAL OPTICS INC., Santa Ana, CA (US)

(72) Inventors: Brooke C. Basinger, Long Beach, CA (US); Daniel J. Urbaniak, Aliso Viejo, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 1 day.

(21) Appl. No.: 14/971,664

(22) Filed: Dec. 16, 2015

(65) Prior Publication Data
US 2016/0106585 A1     Apr. 21, 2016

Related U.S. Application Data

(62) Division of application No. 13/331,005, filed on Dec. 20, 2011, now Pat. No. 9,241,829.

(51) Int. Cl.
*A61F 9/00* (2006.01)
*A61K 9/00* (2006.01)

(52) U.S. Cl.
CPC .......... *A61F 9/0017* (2013.01); *A61K 9/0051* (2013.01)

(58) Field of Classification Search
CPC ............................. A61F 9/0017; A61K 9/0051
See application file for complete search history.

(56) References Cited

U.S. PATENT DOCUMENTS

| 5,098,443 | A | * | 3/1992 | Parel ................... A61F 2/14 128/898 |
| 5,166,331 | A |   | 11/1992 | Della Valle et al. |
| 5,443,505 | A |   | 8/1995 | Wong et al. |
| 7,181,287 | B2 | * | 2/2007 | Greenberg ............ A61N 1/0543 607/116 |
| 8,053,078 | B2 |   | 11/2011 | Hu et al. |
| 8,096,972 | B2 |   | 1/2012 | Varner et al. |
| 8,348,897 | B2 |   | 1/2013 | Shih et al. |
| 2002/0188282 | A1 |   | 12/2002 | Greenberg |
| 2003/0014036 | A1 |   | 1/2003 | Varner et al. |
| 2004/0133155 | A1 |   | 7/2004 | Varner et al. |
| 2005/0101582 | A1 |   | 5/2005 | Lyons et al. |
| 2005/0181017 | A1 |   | 8/2005 | Hughes et al. |
| 2005/0181018 | A1 |   | 8/2005 | Peyman |
| 2006/0024350 | A1 |   | 2/2006 | Varner et al. |
| 2007/0224278 | A1 |   | 9/2007 | Lyons et al. |
| 2008/0027304 | A1 |   | 1/2008 | Pardo et al. |
| 2008/0145407 | A1 | * | 6/2008 | Huang ................ A61K 9/1647 424/428 |
| 2009/0082321 | A1 |   | 3/2009 | Edelman et al. |
| 2009/0149435 | A1 |   | 6/2009 | Wang et al. |
| 2010/0088548 | A1 |   | 4/2010 | Gulwani et al. |
| 2010/0166862 | A1 |   | 7/2010 | Francois et al. |
| 2010/0255061 | A1 |   | 10/2010 | De Juan, Jr. et al. |
| 2011/0125090 | A1 |   | 5/2011 | Peyman |
| 2012/0136322 | A1 |   | 5/2012 | Alster et al. |
| 2013/0046382 | A1 | * | 2/2013 | Mazzocchi ........... A61F 9/0017 623/6.63 |

FOREIGN PATENT DOCUMENTS

| WO | 2011103555 A2 | 8/2011 |
| WO | 2011134146 A1 | 11/2011 |

OTHER PUBLICATIONS

International Search Report for Application No. PCT/US2012/070956, dated May 10, 2013, 7 pages.

* cited by examiner

*Primary Examiner* — Robert A Wax
*Assistant Examiner* — Olga V Tcherkasskaya
(74) *Attorney, Agent, or Firm* — Johnson & Johnson Surgical Vision, Inc.

(57) ABSTRACT

The present invention relates to an apparatus, system and method for, and for providing, intraocular delivery of an active agent. The apparatus, system and method may include an implantable scaffold and an active agent associated with the implantable scaffold. The implantable scaffold and the active agent may be configured to be completely contained within the eye upon implantation. The implantable scaffold may be a mechanical scaffold, or the implantable scaffold may be a chemical scaffold.

24 Claims, 8 Drawing Sheets

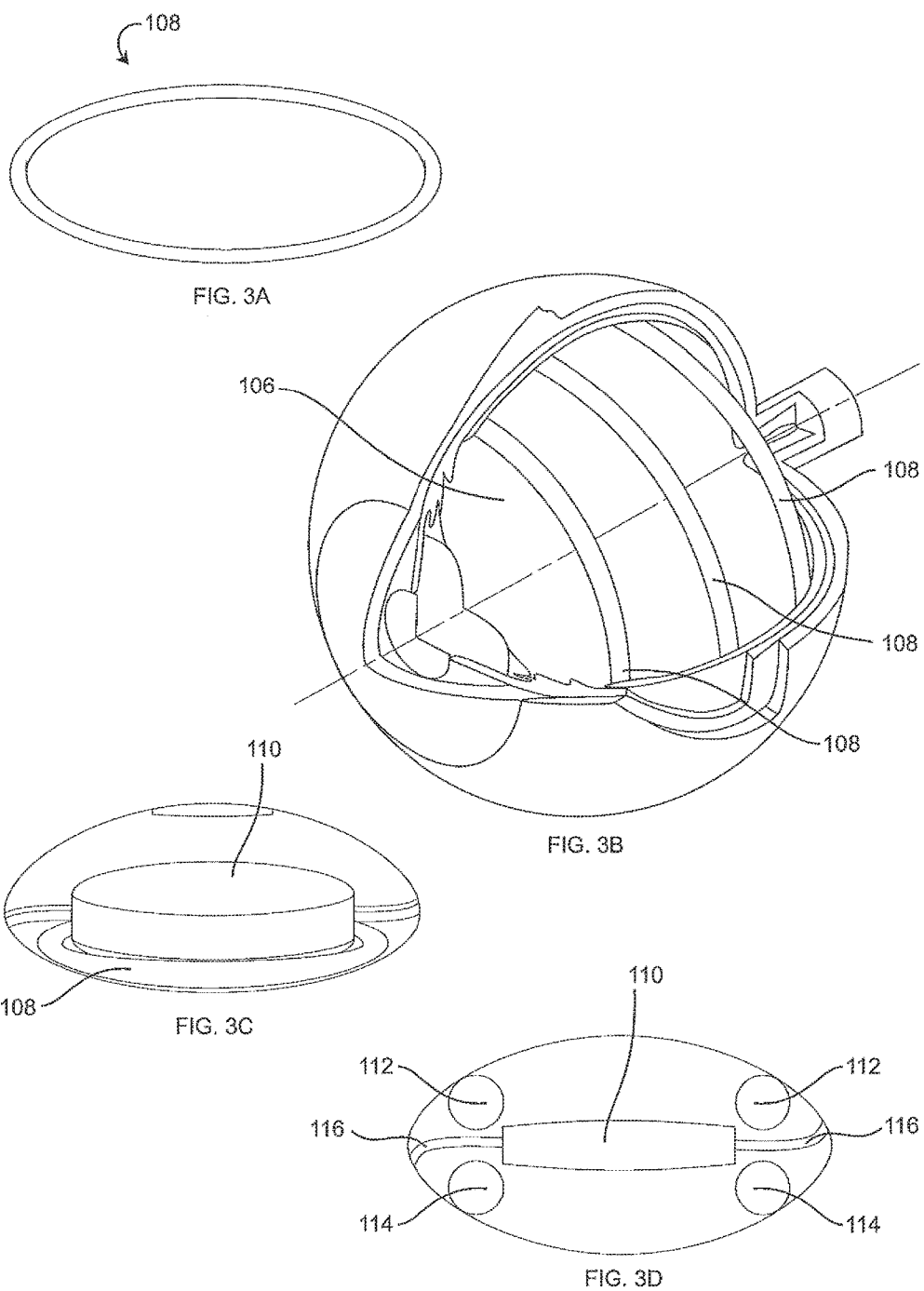

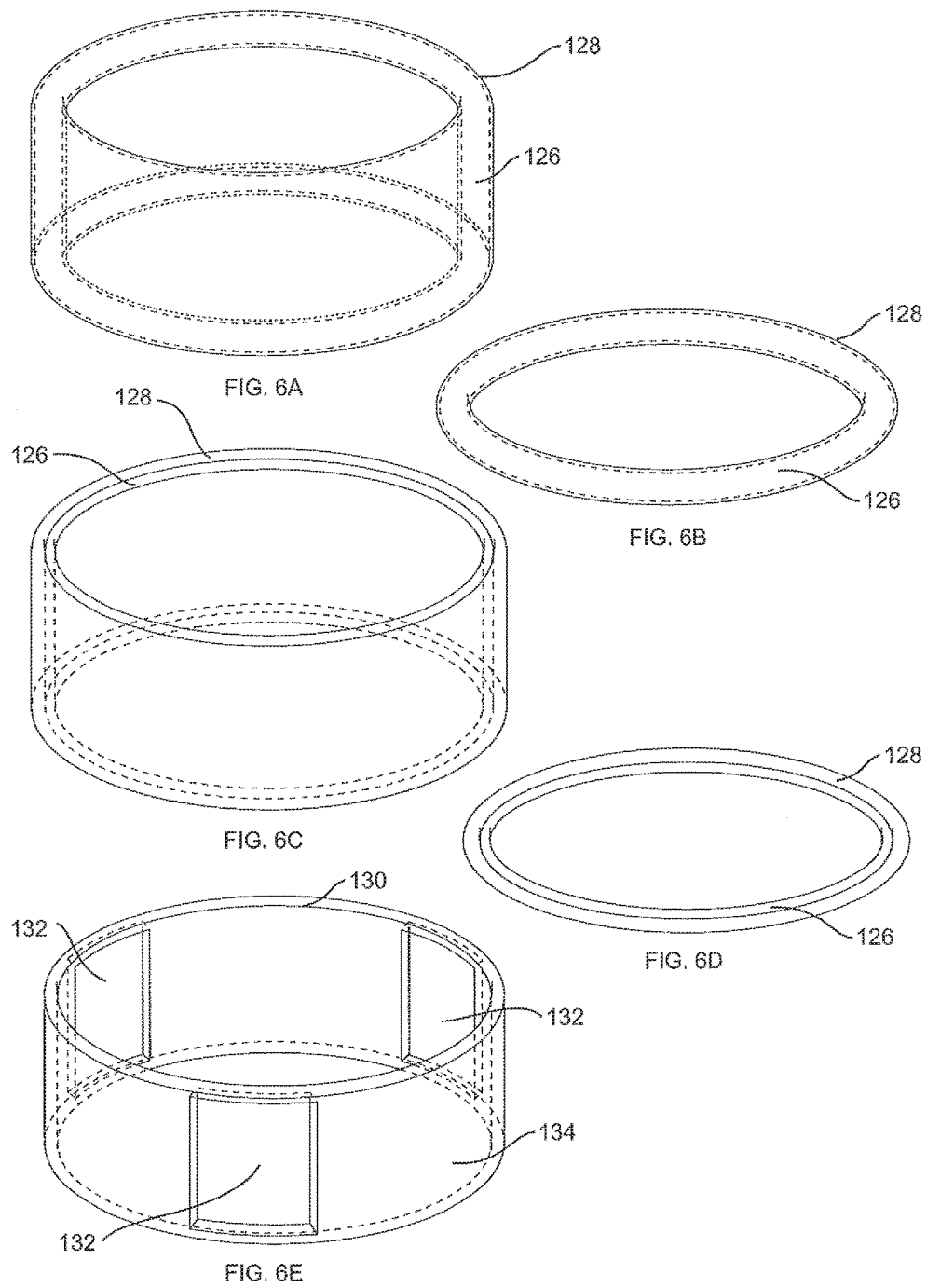

IMPLANTABLE INTRAOCULAR DRUG DELIVERY APPARATUS, SYSTEM AND METHOD

CROSS-REFERENCE TO RELATED APPLICATIONS

This application claims priority to and is a divisional of U.S. application Ser. No. 13/331,005, filed on Dec. 20, 2011, the contents of which is hereby incorporated by reference in its entirety.

FIELD OF THE INVENTION

The field of the present invention relates to systems and methods for delivering an active agent in the eye. More specifically, the field of the present invention relates to implantable apparatuses, systems and methods for delivering an active agent to the intraocular portion of the eye, such as over an extended period of time.

BACKGROUND OF THE INVENTION

Several ocular diseases and conditions can be treated through the administration of active agents, such as pharmaceuticals. For example, retinal diseases including diabetic retinopathy, age-related macular degeneration (AMD) and macular edema can be treated pharmacologically. Furthermore, conditions related to ocular surgery, such as inflammation, infection, and the like can be treated pharmacologically.

However, due to anatomical factors, it is very challenging to deliver an effective concentration of a pharmacologically active agent to interior portions of the eye, particularly when the pharmacologically active substance needs to be administered over an extended period of time.

Various methods have been developed for delivering an active agent to the interior segments of the eye, but all have disadvantages. One currently used method to treat intraocular conditions is delivering the active agent topically to the cornea or sclera. Topical drug delivery is disadvantageous for intraocular portions of the eye, such as the posterior chamber, because the drug must penetrate several layers of tissue before reaching the target area.

Another method for intraocular delivery of an active agent is transcleral delivery, in which the pharmacological agent is introduced through the choroidal blood supply. Similar to topical delivery, transcleral delivery requires that the active agent penetrate several layers of tissue to reach target areas, such as the retina. Furthermore, when treating locations such as the retina, this and other systemic delivery methods must cross the blood/retina barrier, which is disadvantageous because of the relative impermeability of the blood-retina barrier.

The most typical currently-used method to apply a given active agent to the interior of the eye is repeated intravitreal injections. These repeated intravitreal injections are quite uncomfortable for the patient, which leads, in part, to a decrease in patient compliance. Moreover, repeated intravitreal injections carry an increased risk of local side effects and complications, such as corneal abrasions and infection. Attempts to develop methods of avoiding intravitreal injections have also typically presented significant disadvantages.

For example, U.S. Patent Application publication No. 2004/0133155, to Varner et al., discloses devices, such as scleral plugs, for intraocular drug delivery that generally include a coil shaped implant that is positioned in the posterior chamber of the eye with a cap residing outside of the eye.

Further, U.S. Patent Application publication No. 2002/0188282, to Greenberg, discloses implantable drug delivery devices that include an electrode array body in communication with a drug reservoir positioned outside of the eye.

However, a particular disadvantage of drug delivery systems having portions of the systems residing outside of the eye is patient discomfort, and additional disadvantages include increased risk of complications and side effects, such as infection.

Therefore, a need exists to develop alternative systems and methods to deliver an active agent to the internal portions of the eye, particularly when the biologically active agent needs to be administered over an extended period of time.

BRIEF DESCRIPTION OF THE FIGURES

Embodiments of the present invention will be understood with reference to the detailed description in conjunction with the accompanying figures, in which like numerals indicate like aspects, and wherein:

FIG. 3A illustrates a perspective view of a generally ring shaped scaffold according to an embodiment of the present invention; and FIG. 3B illustrates a perspective view of a plurality of generally ring shaped scaffolds implanted into the vitreous body;

FIG. 3C illustrates a perspective view of a generally ring shaped scaffold implanted into the capsular bag in conjunction with an intraocular lens;

FIG. 3D illustrates a perspective view of a plurality of generally ring shaped scaffolds implanted into the capsular bag;

FIG. 6A illustrates a perspective view of a generally cylindrically shaped scaffold having a reservoir positioned within the scaffold according to an embodiment of the present invention;

FIG. 6B illustrates a perspective view of a generally ring shaped scaffold having a reservoir positioned within the scaffold according to an embodiment of the present invention;

FIG. 6C illustrates a perspective view of a generally cylindrically shaped scaffold having a reservoir connected to the exterior of the scaffold according to an embodiment of the present invention;

FIG. 6D illustrates a perspective view of a generally ring shaped scaffold having a reservoir connected to the exterior of the scaffold according to an embodiment of the present invention;

FIG. 6E illustrates a perspective view of a generally cylindrically shaped scaffold having a plurality of independent reservoirs according to an embodiment of the present invention;

SUMMARY OF THE INVENTION

Figure 1A:
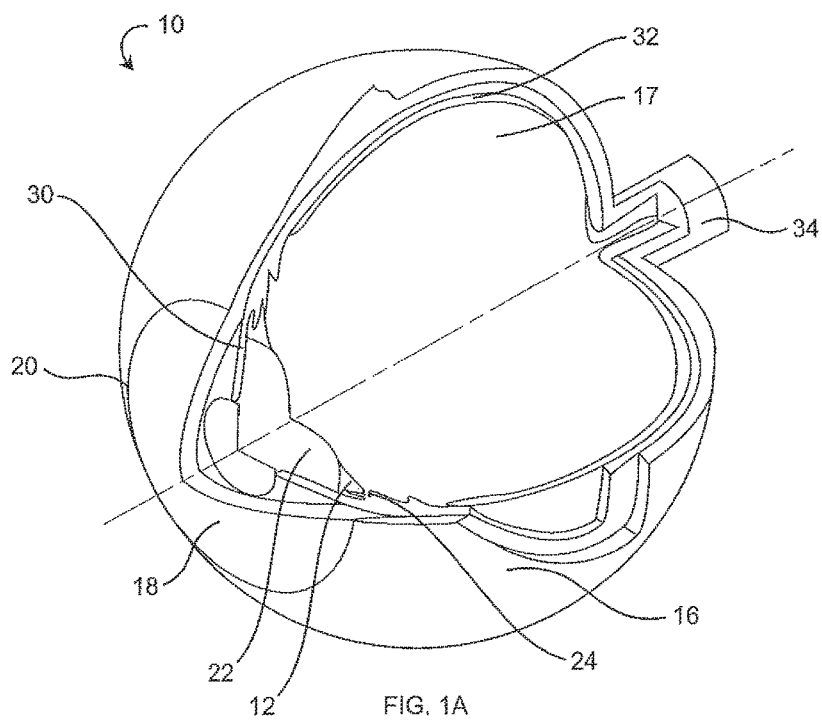
FIG. 1A illustrates a perspective view of an eye with a cut out of the top right corner.

The present invention is and includes at least an apparatus, system and method for, and for providing, intraocular delivery of an active agent. A system in accordance with the present invention may include an implantable scaffold and an active agent associated with the implantable scaffold. In certain exemplary embodiments, the implantable scaffold and the active agent may be configured to be completely contained within the eye upon implantation. In certain exemplary embodiments, the implantable scaffold may be a mechanical scaffold. In other exemplary embodiments, the implantable scaffold may be a chemical scaffold which provides a platform for drug delivery without mechanical interaction with ocular tissues.

An apparatus according to the present invention may be or include an implantable scaffold suitable for intraocular delivery of at least one active agent. The implantable scaffold may include at least one physical vehicle suitable for intraocular implantation, and at least one physical association of the active agent with the at least one physical vehicle. The at least one physical association may include, for example, the physical vehicle exerting physical influence over the active agent, being physically and/or chemically contacted with or bonded to the agent, having a certain releasability of the agent upon physical/chemical decay, or the like. The physical association may be suitable for intraocular delivery of the active agent by the at least one physical vehicle upon the intraocular implantation of at least the physical vehicle, the physical association, and the active agent.

A method of providing intraocular delivery of an active agent according to the present invention may include providing a scaffold suitable for intraocular implantation, associating the active agent with the scaffold, and providing for the delivery of the active agent from the scaffold following the intraocular implantation. In accordance with the method, the active agent may be delivered solely intraocularly following intraocular implantation. Further, the associating may be a mechanical associating, or a chemical associating.

Thus, the present invention provides at least an apparatus, system and method to deliver an active agent to the internal portions of the eye, particularly when the biologically active agent is to be administered over an extended period of time. These and other advantages of the present invention will become apparent to those skilled in the art from the following detailed description of the invention and the accompanying drawings.

DETAILED DESCRIPTION OF EMBODIMENTS

It is to be understood that the figures and descriptions of the present invention have been simplified to illustrate elements that are relevant for a clear understanding of the present invention, while eliminating, for the purpose of clarity and brevity, many other elements found in typical drug delivery apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

"Scaffold," as used herein, refers at least to any material that provides a physical vehicle having the principal purpose of delivering a pharmacologically active agent into the interior portions of the eye, and that provides such a vehicle for at least substantially complete implantation into the eye.

"Mechanical Scaffold," as used herein, refers to a scaffold in which at least a portion of the scaffold is used for the purpose of delivering an active agent, and in which at least a portion of the scaffold is independent from the active agent. A mechanical scaffold may impart or otherwise define a physical dimension that is independent of the active agent.

"Chemical Scaffold," as used herein, refers to a scaffold for which the physicality of the scaffold may be substantially formed of aspects of the active agent to be delivered. For example, a chemical scaffold may include a scaffold where at least a portion of the scaffold chemically interacts with an active agent, which may include physical interaction, formation of a chemical bond, or both.

It is to be understood that a scaffold may be both a mechanical and a chemical scaffold and may also change principally from a chemical scaffold to a mechanical scaffold or vice versa at a given point in time after implantation.

"Polysaccharide," as used herein, refers to a polymer of more than two monosaccharide molecules, of which the monosaccharides can be identical or different.

I. Anatomy of the Eye

Figure 1B:
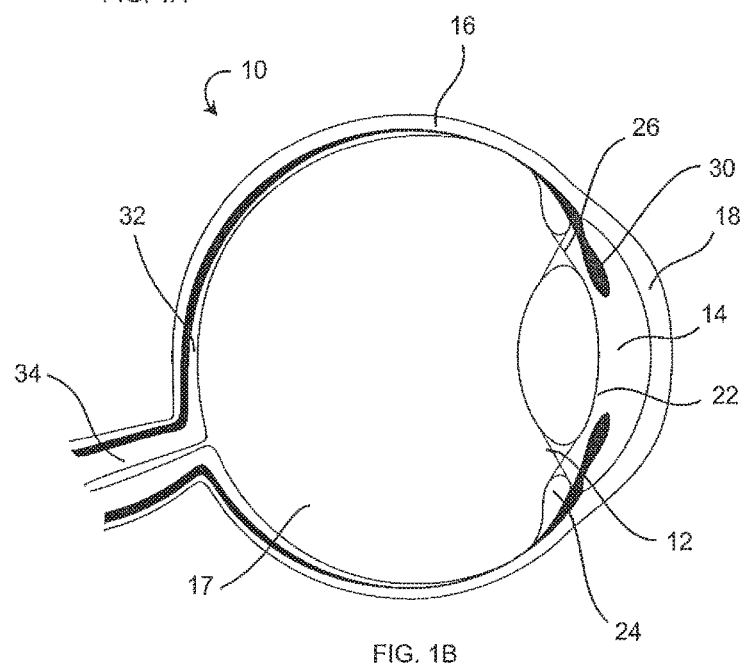
FIG. 1B illustrates a cross section of the eye in FIG. 1A.

The apparatuses, systems and methods described herein may be better understood with a background discussion on the anatomy of the eye. Referring to FIGS. 1A and 1B, FIG. 1A illustrates a perspective view of an eye 10, with a cut out of the top right corner for illustrative purposes. FIG. 1B is a cross section of eye in FIG. 1A, taken down the middle of the eye. As illustrated in both FIGS. 1A and 1B, the eye 10 may be conceptualized as a fluid filled ball having two chambers, a posterior chamber 12 and an anterior chamber 14. The sclera 16 surrounds the posterior chamber 12. In the posterior chamber 12 is the vitreous body 17, which is filled with a viscous fluid known as vitreous humor. The cornea 18 encloses the anterior chamber 14, which is filled with a fluid known as aqueous humor. The cornea 18 meets the sclera 16 at the limbus 20. Located between the anterior 14 and the posterior chamber 12 is the capsular bag 22. The capsular bag 22 is connected to an annular ciliary muscle 24 by suspensory ligaments, or zonules, 26. The capsular bag 22 contains a crystalline lens which transmits light passing through the orifice of the iris 30 to the retina 32. The retina 32 surrounds the majority of the posterior chamber 12. At the rear of the posterior chamber 12 is the optic nerve 34.

II. The Scaffold

Certain embodiments of the present invention include a system for intraocular delivery of a pharmacologically active agent (also referred to herein as "active agent") comprising a scaffold and an active agent. In particular exemplary embodiments of the present invention, the scaffold may at least partially comprise the active agent, and in other exemplary embodiments the scaffold may be distinct from the active agent.

The scaffold described herein is preferably configured for at least substantial insertion into the intraocular segments of the eye. The scaffold may be a mechanical or a chemical scaffold, or a combination thereof. In certain embodiments more than one scaffold may be positioned in multiple locations within the eye. Multiple scaffolds may be used to treat more than one condition, or the multiple scaffolds can treat a single condition by delivering one or more, potentially different, active agents. When more than one scaffold is used, the scaffolds may be the same or different.

1. Mechanical Scaffold

Brief Description of the Mechanical Scaffold

A mechanical scaffold may be formed into any number of different shapes. It is to be appreciated that the particular shape of the mechanical scaffold may be optimized according to the particular placement within the eye, for the convenience of implantation into the eye, or for like reasons. Irrespective of the shape the mechanical scaffold takes, the mechanical scaffold should not interfere with the visual axis of the eye after implantation. For example, the mechanical scaffold may provide sufficient structure to keep the drug delivery system from interfering with the visual axis. However, if the mechanical scaffold is configured such that light is not distorted when passing through at least a portion of the mechanical scaffold, the mechanical scaffold may be positioned so that at least part of the visual axis may pass through the non-distorting portion of the mechanical scaffold.

Figure 2A:
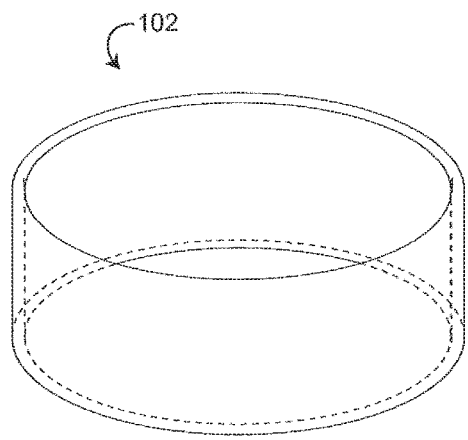
FIG. 2A illustrates a perspective view of generally cyclindrically shaped scaffold according to an embodiment of the present invention.
Figure 2B:
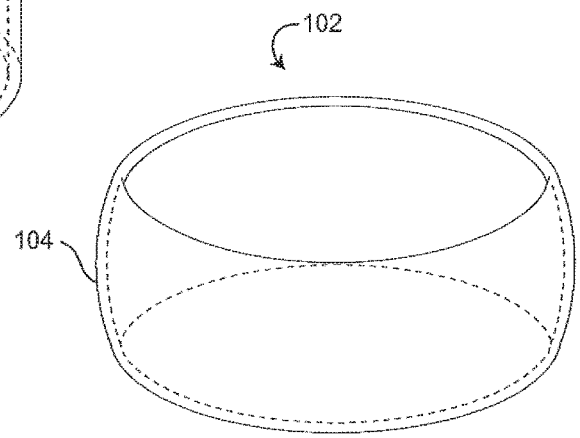
FIG. 2B illustrates a perspective view of generally cyclindrically shaped scaffold having convex shaped walls according to an embodiment of the present invention.
Figure 2C:
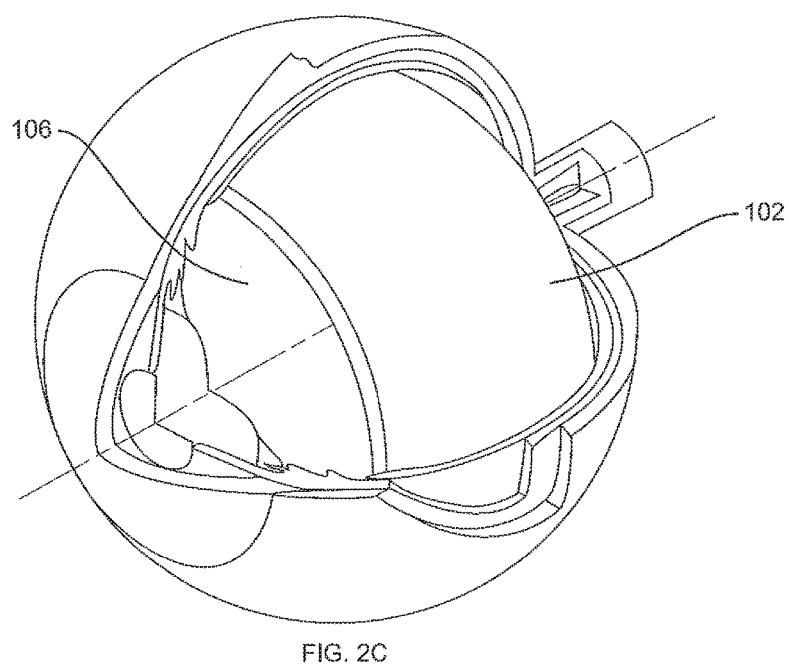
FIG. 2C illustrates a perspective view of a generally cyclindrically shaped scaffold implanted into the vitreous body.

FIG. 2A illustrates an example of a delivery system that includes a generally cylindrically shaped mechanical scaffold 102. For example, such a generally cylindrical shape may be useful when the delivery system is to be implanted into the vitreous body, which is generally spherical. In some embodiments, and as more particularly illustrated in FIG. 2B, the walls 104 of a generally cylindrically shaped mechanical scaffold 102 may have a convex shape so as to compliment the concave shape of an interior chamber of the eye, such as the vitreous body. It is to be understood that the degree of curvature of the walls 104 of a generally cylindrical scaffold may be optimized to compliment the dimensions of the desired location of implantation. FIG. 2C is a perspective view of an eye illustrating a generally cylindrical mechanical scaffold 102 after implantation into the vitreous body 106.

The height of the walls 104 of a generally cylindrical mechanical scaffold may be optimized depending on the particular chamber of the eye that the mechanical scaffold is to be implanted, and/or depending upon the implantation location or methodology, for example. Accordingly, in some embodiments, the height of the walls of a generally cylindrical mechanical scaffold may be 1 to 18 mm, by way of non-limiting example.

In certain exemplary embodiments and as particularly illustrated in FIG. 3A, the delivery system may include a generally ring shaped mechanical scaffold 108. Similar to the embodiments described above, a generally ring shaped mechanical scaffold may be useful when the delivery system is to be implanted into the vitreous body. For example, FIG. 3B illustrates a perspective view of an eye that includes a plurality of generally ring shaped mechanical scaffolds 108 implanted into the vitreous body 106. In other embodiments, a generally ring shaped mechanical scaffold may be useful wherein the delivery system is to be implanted within the capsular bag. For example, FIG. 3C illustrates a perspective view of an exemplary embodiment wherein a generally ring shaped mechanical 108 scaffold is implanted surrounding an IOL 110 in the capsular bag. FIG. 3D illustrates a cross section view of a capsular bag in which an upper generally ring shaped mechanical scaffold 112 and a lower generally ring shaped mechanical scaffold 114 are positioned above and below the haptics 116 of an IOL 110, respectively.

The exact dimensions of a generally ring shaped scaffold may be optimized depending on the particular segment of the eye that the mechanical scaffold is to be implanted, the age of the patient and thus the overall size of the eye, and/or depending upon the implantation location or methodology, for example. Further, the dimensions of a scaffold as discussed herein may be dependent on the type or amount of active agent to be delivered, and to which location(s) of the eye the delivery is to occur. It is to be understood that the scaffold may take any form, size, or shape to accommodate any portion of any eye. In some particular embodiments, the outside diameter of a generally ring shaped mechanical scaffold may be 22 to 24 mm, by way of non-limiting example.

Figure 4A:
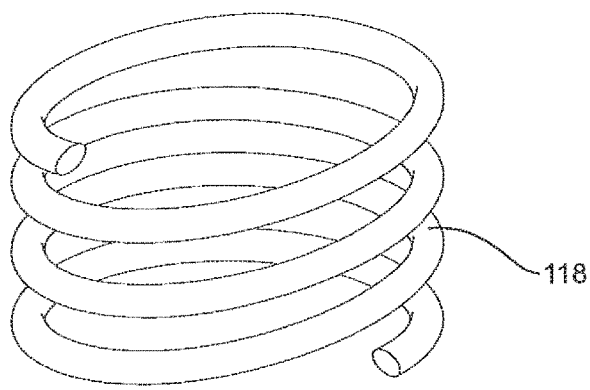
FIG. 4A illustrates a perspective view of a generally helically shaped scaffold according to an embodiment of the present invention.
Figure 4B:
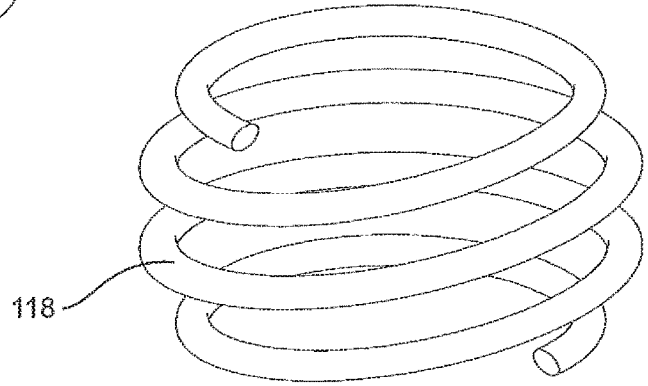
FIG. 4B illustrates a perspective view of a generally helically shaped scaffold having a shape complimentary to the vitreous body according to an embodiment of the present invention.

In further embodiments, and as more particularly illustrated in FIG. 4A, the delivery system may include a generally helical shaped mechanical scaffold 118 after implantation into the eye. In such embodiments, the mechanical scaffold may initially be formed into a tubular shape that may subsequently form the generally helical shape after implantation, such as wherein a tubular shaped scaffold is wrapped around the interior wall of the desired segment of the eye. In some embodiments, and as particularly illustrated in FIG. 4B, the generally helical shaped scaffold 118 may be formed so as to compliment an interior segment of the eye, such as the vitreous body 106.

Figure 5A:
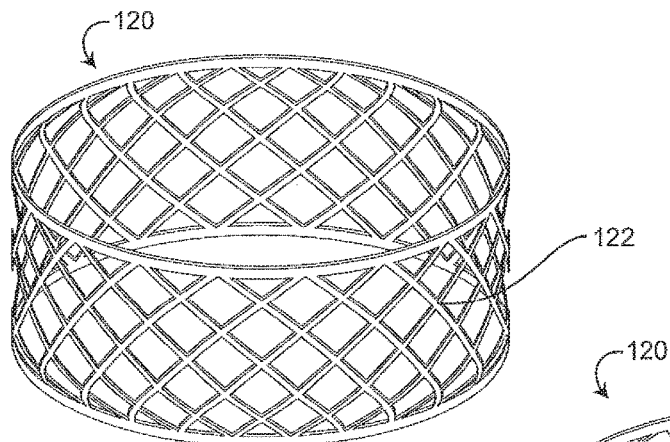
FIG. 5A illustrates a perspective view of a generally cylindrically shaped scaffold having a mesh structure according to an embodiment of the present invention.
Figure 5B:
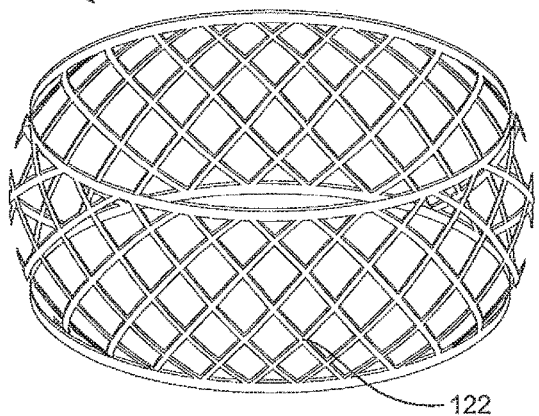
FIG. 5B illustrates a perspective view of a generally cylindrically shaped scaffold having a convex mesh structure according to an embodiment of the present invention.
Figure 5C:
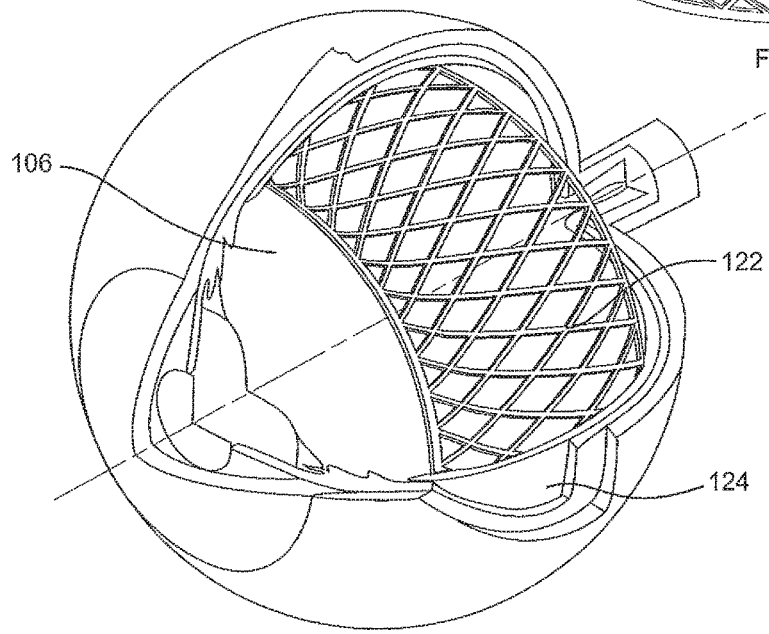
FIG. 5C illustrates a perspective view of a generally cylindrically shaped scaffold having a convex mesh structure implanted into the vitreous body according to an embodiment of the present invention.

In the embodiments illustrated above, the mechanical scaffold is shown as having a solid structure. However, it is to be understood that any structure or shape may be employed. For example, in certain exemplary embodiments, and as particularly illustrated in FIG. 5A, the mechanical scaffold 120 may have a cage or mesh like structure 122. Similar to embodiments discussed above, the walls of a cage or mesh like structure may complement the shape of the desired area of implantation, such as, for example, a convex shape. FIG. 5C illustrates a cage or mesh like structured scaffold 122 implanted into the vitreous body 106. The cage or mesh like structure 122 may be advantageous in certain embodiments, for example, when implanted into the vitreous body 106, at least because, in such an embodiment, a smaller amount of surface area of the mechanical scaffold would make contact with and potentially exert pressure on the retina 124.

The mechanical scaffold may be constructed from any material that can be safely implanted into the eye. For example, the mechanical scaffold may be constructed from a polymer, a metal, ceramics, or a combination thereof. By way of more particular example, the mechanical scaffold may be constructed from materials including, but not limited to, nitinol, polyimide, platinum, stainless steel, molybdenum, gold, polyvinylidene fluoride, silicone, polytetrafluoroethylene, expanded polytetrafluoroethylene, differential fluoropolymer, fluorinated ethylene propylene, prolene/polyolefins, polypropylene, poly(methyl methacrylate), acrylic, polyethylene terephthalate, polyethylene, polylactide, parylene, nylon (polyamide), polyether ether ketone, polysulfone, polyamideimides, polyether block amides, polyurethanes, thermoplastic elastomers (such as Kraton), liquid crystal polymers, and combinations thereof.

In some embodiments, the mechanical scaffold may be made from a material that is sufficiently flexible so that it can be bent, folded, and/or compressed for insertion in the eye. Consequently, only a small incision (relative to the size of the mechanical scaffold) would be needed to implant the mechanical scaffold. However, in any such embodiment, the pressure limitations of a properly functional eye must not be exceeded.

In certain embodiments, the mechanical scaffold may be made from a material that self-expands and/or has shape memory after implantation into the eye. For example, an exemplary material which can self-expand or have shape memory after implantation into the eye includes, but is not limited to, nitinol. However, in any such embodiment, the pressure limitations of a properly functional eye must not be exceeded.

In certain embodiments, the scaffold may be made from a material that is capable of being physically expanded and retaining its expanded shape. Suitable materials, which may be physically expanded and able to retain their expanded shape, include but are not limited to, polymers and metals. However, in any such embodiment, the pressure limitations of a properly functional eye must not be exceeded.

In certain embodiments, at least the portion of the mechanical scaffold which contacts the body may be made from a material that is bioabsorbable, i.e., capable of being absorbed into the body after implantation. For example, materials which can be absorbed into the body include, but are not limited to, polyglycolic acid (PGA), polylactic acid (PLA), and/or copolymers thereof. The rate at which the scaffold is absorbed into the body may be optimized by methods known to the skilled artisan. For example, in some embodiments the delivery system may further include an inhibitor or accelerator that may change the rate at which a bioabsorbable material would otherwise degrade. As an additional example, the drug delivery system may further include an inhibitor or accelerator to bioabsorability that may be configured to be released or activated after there is no further need for the intraocular delivery of drugs.

In alternate embodiments, the mechanical scaffold may not be bioabsorbable. In such embodiments, the mechanical scaffold may be a permanent implant into the eye, or may be configured such that it may be removed from the eye, dissolved in the eye, or the like, such as after implantation and/or service of purpose. For example, in some embodiments, the mechanical scaffold may be constructed from a material that will degrade only when contacted with a particular compound. The particular compound may then be contacted with mechanical scaffold while still in the eye, such as by injection, absorption, or the like, preferably after intraocular active agent delivery is no longer needed.

In certain embodiments, the mechanical scaffold may include a reservoir. As used herein, a reservoir means any structure that can releasably contain an active agent. In some embodiments, and as more particularly shown in the exemplary embodiments of FIGS. 6A and 6B, the reservoir may be contained at least partially within, substantially within, or entirely outside the mechanical scaffold. FIG. 6A-6B illustrates a generally cylindrically shaped mechanical scaffold 128 and a generally ring shaped scaffold, respectively, that include a reservoir 126 contained within the mechanical scaffold. In other exemplary embodiments, and as particularly illustrated in FIG. 6C and 6D, the reservoir 126 may be a separate element that may be connected to the mechanical scaffold 128. It is to be understood that the exact selection of the placement and area of formation of the reservoir in relation to the scaffold may be dependent upon a number of factors, including the desired location of implantation, the methodology of implantation, and/or the localized or overall pressure considerations in relation to the eye, for example.

It is to be further understood that in the exemplary embodiments described herein, the reservoir may be made from the same or a different material than the mechanical scaffold. For example, in particular embodiments the reservoir may be made from a flexible material of which the volume may be expanded when filled with the active agent. In other words, in certain embodiments the reservoir may be inflatable.

It is to be understood that there may be one or more reservoir(s) with one or more scaffold(s). For example, FIG. 6E illustrates a mechanical scaffold 130 having three separate reservoirs 132. The reservoirs 132 may be entirely separated, as illustrated, or one reservoir may be configured to include discrete zones which are separated from each other, for example, by partitions 134.

The position of the reservoir(s) within the scaffold and subsequently within the eye may be selected so as to deliver the active agent in close proximity to the desired area of treatment, or proximate to, or predeterminately remote from, any location which is to be effectuated by the desired release profile of the active agent. For example, as understood by the skilled artisan, fluids inside the vitreous body may exhibit a patterned flow. Therefore, it may be desirable to locate the reservoir in a position away from the desired area of treatment so that the active agent can migrate to the desired area of treatment through the patterned flow of the fluids.

In certain exemplary embodiments, the one or more reservoir(s) may be configured to hold one or more active agents. For example, in embodiments in which more than one reservoir is used, each reservoir may contain the same or different active agents. It is to be understood that the exact number, contents, and location of the reservoir may be optimized depending upon the implantation location, methodology, intended effects, or pressure limitations of the eye, for example.

Figure 7:
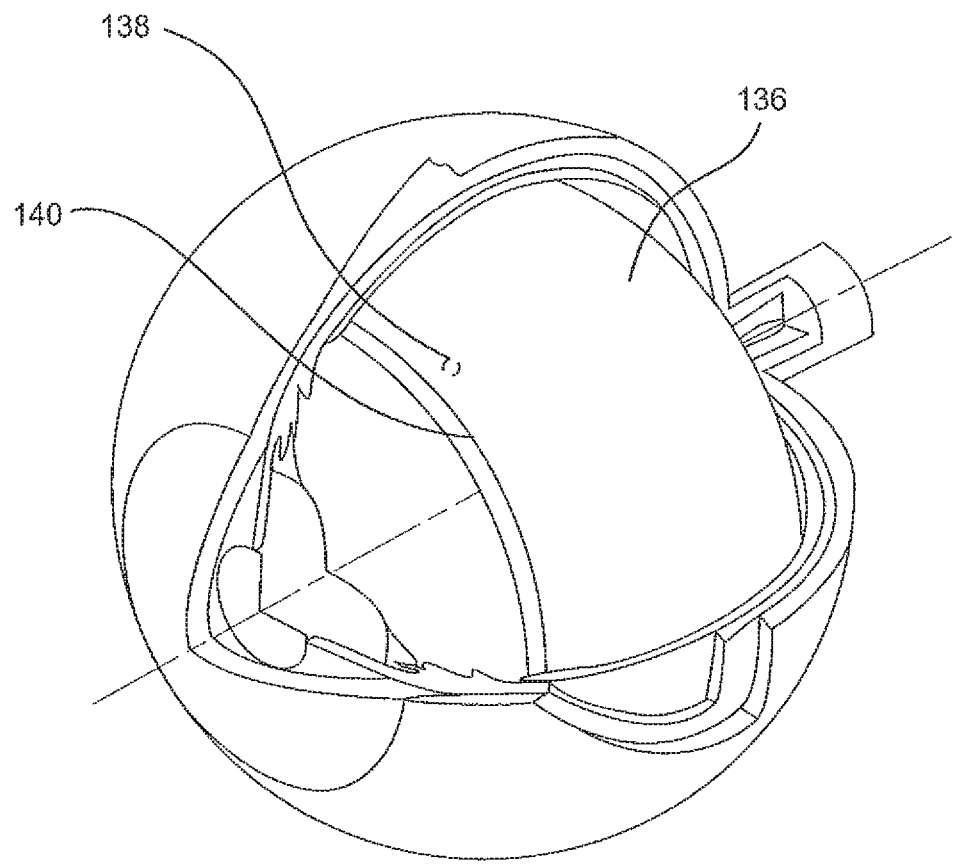
FIG. 7 illustrates a perspective view of a generally cylindrically shaped scaffold implanted in the vitreous body and including an insertion point to allow the reservoir to be filled and/or refilled according to an embodiment of the present invention.

In certain embodiments, the reservoir may be configured to be filled and/or refilled after implantation into the eye. For example, FIG. 7 illustrates an exemplary embodiment wherein the scaffold 136 includes an insertion port 138 that enables the reservoir 140 to be filled or refilled through an injection during and/or after implantation into the eye. In certain embodiments, the insertion port may be located such that it may be readily accessed through the same injection site used to implant the drug delivery system. For example, when the drug delivery system is to be inserted in the posterior chamber of the eye, the location of the insertion port may be such that the insertion port can be accessed through an injection beginning in the pars plana. In such embodiments, as illustrated in FIG. 7, the insertion port may be located on the wall of the reservoir that is closest to the visual axis. Additionally and/or alternatively, an insertion point may be located on the wall of the reservoir that is closest to the interior wall of the posterior chamber. It should be appreciated that the exact location of the insertion port may be optimized based on the particular location of implantation and orientation of the delivery system.

In certain embodiments, the reservoir may be positioned outside of the eye and held in place, for example, by a suture. In such embodiments, the reservoir may be in fluid communication with the scaffold and/or an interior positioned reservoir. The fluid communication may be effected, for example, with a transscleral tube. In such embodiments, the external reservoir may continuously provide additional active agent to the scaffold and/or the interior reservoir, and/or may be at least partially activated through an external pressure, such as lightly pressing on the external reservoir.

In certain exemplary embodiments, particularly embodiments employing a reservoir, the reservoir or active agent-infused scaffold may be at least partially empty, or lacking at least one desired active agent, prior to insertion into the eye, and may be filled by the surgeon either before or after the scaffold is positioned in the desired location.

In certain embodiments, the scaffold and/or reservoir may further include one or more caps. The cap may be a particular segment of the scaffold and/or reservoir or may be an additional component. For example, in certain embodiments, the scaffold and/or reservoir may be constructed with one or more apertures as described above which are plugged with caps. The caps may be installed with the scaffold prior to implantation, or in some embodiments, the cap may be installed, for example, in the insertion port after filling the scaffold/and or reservoir with an active agent.

In certain embodiments, the one or more caps may be configured to have a thickness and/or density that allows an active agent to diffuse through the cap and be released into the eye. It is to be understood that the exact size, thickness, and/or density of the cap may be selected to achieve the desired elution profile.

In some embodiments, at least a portion of the one or more caps may be made from a material that is capable of degrading over time such that a small aperture may be formed thereby allowing an active agent to be initially released through the cap at a desired point in time after implantation. The size of the aperture may continue to increase while the cap is continuing to degrade such that the active agent may be release in larger quantities and/or in a faster time. In particular embodiments, the one or more caps may have varying thicknesses such that varying elution profiles may be obtained. For example, a first cap may have a smaller thickness and/or density than a second cap, such that an active agent is first released through the first cap.

In certain embodiments, for example, the cap may be made from any material that the scaffold and/or reservoir may be made from. In particular embodiments, the cap may be constructed from a polymer such as polyglycolic acid (PGA), polylactic acid (PLA), and/or copolymers thereof, for example.

It is to be understood that any combination of materials, thicknesses, quantity, and density of the one or more caps may be used to obtain the desired elution profile.

Release of the Active Agent from a Mechanical Scaffold

In addition to the scaffold, the drug delivery systems and methods disclosed herein further include an active agent. The active agent may be connected to and/or contained within the mechanical scaffold and/or the reservoir (if present). The scaffold and/or the reservoir may be configured to release the active agent substantially as a single dose, or more preferably over a desired period of time. The active agent may be released from the scaffold and/or the reservoir in a number of ways, including, but not limited to: a plurality of apertures; diffusion of the active agent; degradation of the scaffold and/or reservoir having an active agent connected thereto; degradation of a coating having an active agent connected thereto; or a combination thereof.

Figure 8A:
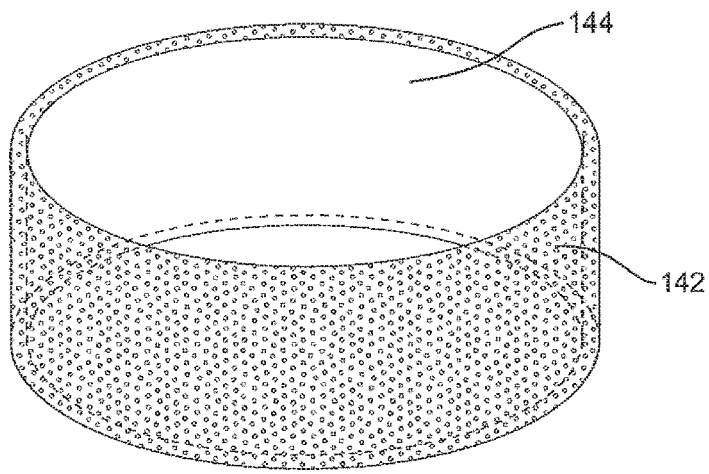
FIG. 8A illustrates a perspective view of a generally cylindrically shaped scaffold having a plurality of apertures to allow the release of the active agent from the reservoir according to an embodiment of the present invention.
Figure 8B:
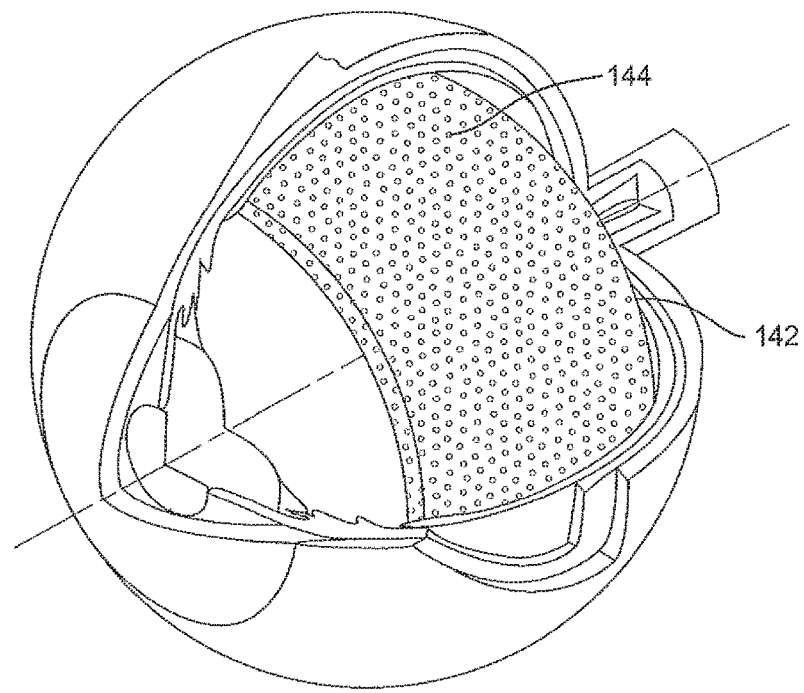
FIG. 8B illustrates a perspective view of a generally cylindrically shaped scaffold having a plurality of apertures implanted into the vitreous body according to an embodiment of the invention.

As illustrated in FIG. 8A and 8B, the scaffold and/or the reservoir 144 may contain a plurality of apertures 142 that allow the active agent to be released from the scaffold and/or the reservoir 144. The size and position of the plurality of apertures 142 may be selected so as to control the rate of release the particular active agent in desired areas. Those skilled in the pertinent arts will appreciate, in light of the discussion herein, that the aperture size, which may be correspondent to the rate of release, may be fixed following implantation, or may be modified after implantation, such as upon increase in the aperture size in accordance with, for example, a degradation rate of the scaffold, or upon decrease of the aperture size responsive to, for example, pressure exerted by forces within the eye upon the scaffold.

The particular shape, quantity, and pattern of the apertures may be selected based on a number of factors including, but not limited to, 1) the desired rate of release of the active agent, 2) the molecular size of the active agent, 3) the location to be targeted for treatment, etc. In certain embodiments, an exemplary diameter of the apertures may be from 1 to 8 nm, by way of non-limiting example.

The apertures may be created in the scaffold by any method known to the skilled artisan. For example, the apertures may be created by etching, machining, nano-machining, or micro-machining, or in any like manner. Additionally, it may be preferable that, in such aperture-based embodiments, reservoir-based embodiments, and/or like embodiments in which the active agent is released, the scaffold and/or the reservoir be filled with the active agent prior to implantation of the scaffold.

In certain embodiments, and as discussed above, at least a portion of the scaffold and/or reservoir may be made from a material which degrades over time. In such embodiments, the active agent may be attached to the scaffold and/or reservoir by any method. For example, the active agent may be attached to the scaffold and/or reservoir by covalent bonding, ionic bonding, hydrogen bonding, van der waal forces, or combinations thereof. In particular embodiments, covalent bonding, ionic bonding, and/or hydrogen bonding may be further enhanced by van der waal forces. By having the active agent connected to the scaffold and/or reservoir, degradation of the scaffold and/or reservoir releases the active agent. The rate of release of the active agent may then be tied to the rate of degradation of the scaffold and/or the reservoir.

Similar to above, the drug delivery system may include a coating which comprises the active agent. The coating may be applied to the scaffold and/or the reservoir. The coating may be any composition that releasably contains an active agent. Similar to above, the degradation of the coating may control the rate of release of the active agent.

In certain embodiments, the scaffold and/or the reservoir may be configured so that the active agent may diffuse through the scaffold and/or the reservoir. For example, the scaffold and/or reservoir may be constructed from a cross-linked network of polymers. The level of cross-linking may be configured to achieve a desired structure of the polymers that allow an active agent of a particular molecular size to diffuse through the cross-linked network of polymers.

The rate of release of the active agent may be optimized based on the particular condition to be treated and the desired length of time that treatment is desired. The particular release or elution profile for a particular active agent may be chosen so as to obtain a desired therapeutic result. For example, the release profile may be selected such that an initial active agent may be released for one to two days followed by an active agent that is released over a period of months to years. For example, in aperture-based embodiments, it is to be understood that the placement and size of the apertures can be varied to control the release profile of an active agent. A particular advantage of certain embodiments is the ability for the delivery systems to provide sustained release for an extended period of time, such as a number of years. In some embodiments, the delivery system may be refilled periodically to extend the release profile of the active agent.

In exemplary embodiments, at least a partial release of the active agent may be affected by movement of various structures within the eye. For example, if the delivery system is implanted into the lens capsule, a flexible scaffold having a reservoir with apertures may use the natural movement of the zonules of the eye to essentially act as a pump, so as to provide brief, periodic increases in pressure within the scaffold and/or reservoir, thereby releasing a greater amount of the active agent during such brief, periodic instances.

In certain embodiments, the release of the active agent may be responsive to the existent, level or severity of a condition or disease within the eye, i.e., the release amount or schedule may be part of a bio-feedback loop. For example, the scaffold may be configured to release a larger amount of an active substance in response to a condition within the eye, such as glaucoma, which increases intraocular pressure. This could be accomplished, for example, by having a reservoir and/or the scaffold constructed from a flexible material. In this way, external pressure created by inflammation causes a squeezing of the reservoir, thereby causing the active agent to be released through the apertures at an increased rate. Another example of having the release of the active agent be responsive to a condition within the eye could be having the scaffold configured to degrade at an increased rate in the presence of a compound that corresponds to a condition or disease of the eye.

In addition to the rate of release of the active agent from the scaffold and/or reservoir, the delivery systems described herein may include a filter that at least partially covers the trebecular area. The filter may be configured to at least partially block a particular active agent from entering the trebecular area. The trebecular area is the natural irrigation route for fluid in the eye. By at least partially covering the trebecular area with a filter, the active agent that is released from the scaffold and/or reservoir may have a longer time to come into intimate contact with the desired area(s) of treatment, thereby further increasing the release profile and the success of treatment.

2. Chemical Scaffold

Certain embodiments of the present invention include a system for intraocular delivery of an active agent comprising a chemical scaffold having an active agent.

In certain embodiments, the chemical scaffold may be a composition comprising a biodegradable polymer, such that the composition does not have to be removed after the active agent is depleted. Examples of suitable specific classes of biodegradable polymers include, e.g., polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, block copolymers, multi-block co-polymers, multi-block co-polymers with polyethylene glycol (PEG), polyols, terpolymers and mixtures thereof. In exemplary embodiments, the biodegradable polymer may be a polysaccharide.

Suitable polysaccharides include a natural biodegradable polysaccharide, which refers to a non-synthetic polysaccharide that is capable of being enzymatically degraded. Natural biodegradable polysaccharides include polysaccharide and/or polysaccharide derivatives that are obtained from natural sources, such as plants or animals. Natural biodegradable polysaccharides include any polysaccharide that has been processed or modified from a natural biodegradable polysaccharide (for example, maltodextrin is a natural biodegradable polysaccharide that is processed from starch). Exemplary natural biodegradable polysaccharides include maltodextrin, amylose, cyclodextrin, polyalditol, hyaluronic acid, dextran, heparin, chondroitin sulfate, dermatan sulfate, heparan sulfate, keratan sulfate, dextran, dextran sulfate, pentosan polysulfate, and chitosan. Particularly suitable biodegradable polysaccharides include hyaluronic acid. The natural biodegradable polysaccharide can be branched, a substantially non-branched or completely non-branched polysaccharide. In certain embodiments the biodegradable polymer contains functional side groups. For example, the biodegradable polymer may contain carboxylic acid groups, hydroxyl groups, or a combination thereof.

Hyaluronic acid ("HA") is a polysaccharide made by various body tissues. U.S. Pat. No. 5,166,331 discusses purification of different fractions of hyaluronic acid for use as a substitute for intraocular fluids and as a topical ophthalmic drug carrier. Other U.S. patent applications which discuss ocular uses of hyaluronic acid include Ser. Nos. 11/859,627; 11/952,927; 10/966,764; 11/741,366; and 11/039,192.

The biodegradable polymer can be present in the composition in any suitable and effective amount. In some embodiments, the particular amount of biodegradable polymer is selected to achieve the desired release profile. For example, a lower amount of the biodegradable polymer may release an active agent for a shorter period of time, such as one to two days, while a higher amount of biodegradable polymer may release an active agent for a longer period of time, such as one to two years.

In an embodiment, the composition may be a homogenous or heterogeneous suspension, such that the active agent is dispersed (i.e., undissolved, unsolubilized and/or suspended) throughout the composition. In one embodiment, a viscous gel can be formed from the polymer. In another embodiment, a viscous gel can be formed upon cooling the polymer. In other embodiments, the polymer forms a composition that is not gelled.

The composition can have a viscosity of, for example, less than 5000 cP at room temperature. Although viscous, the composition can be formulated as an injectable delivery system, through a needle. As such, the composition can be flowable and can be formulated for injection through, e.g., a 25 gauge needle, or a higher gauge needle (e.g., a 30 gauge needle). It is to be understood that the viscosity of the composition can be increased after injection into the desired intraocular segment. The volume of the delivery system can be selected depending on the available volume in the desired area of implantation. For example, suitable injection volumes can be about 10 µL to about 100 µL, or about 0.01 mL to about 2.0 mL.

In certain embodiments, the chemical scaffold may be a hydrogel or a colloidal gel formed as a dispersion in water, or in other aqueous medium, or mixed with a suitable solvent. Additionally, in certain exemplary embodiments, the biodegradable polymer may have an average molecular weight (pre-cross-linking) of about 700 kDa or greater, and more particularly 1000 kDa or greater, by way of non-limiting example.

The biodegradable polymer material may be cross-linked so as to give the composition a desired level of dimensional stability. For example, the level of cross-linking may be selected so as to achieve the desired level of gelation or viscosity. In certain embodiments, for example wherein the biodegradable polymer contains functional side groups, the biodegradable polymer may be cross-linked through carboxylic acid groups, hydroxyl groups, or a combination thereof, for example. In embodiments wherein the biodegradable polymeris cross-linked through carboxylic acid groups, the polymeric gel may be cross-linked with aziridine cross-linkers, carbodiimide cross-linkers, by esterification with hydroxyl groups, or a combination thereof, for example. In embodiments wherein the biodegradable polymeris cross-linked through hydroxyl groups, cross-linking may occur through esterification with carboxyls. The biodegradable polymer may be cross-linked prior to implantation or may be cross-linked in-vivo.

The chemical scaffold described herein comprises an active agent that is associated with the chemical scaffold. In certain embodiments, the active agent may be connected, physically or chemically, and directly or indirectly, to the chemical scaffold. For example, the active agent may be connected to the chemical scaffold so as to release the biologically active agent as a substantially single dose, or over an extended length of time.

In certain embodiments, the active agent may be connected to the chemical scaffold by covalent bonding, ionic coupling, hydrogen boding, van der waals forces, or a combination thereof. In particular embodiments wherein release of the active agent occurs through hydrolytic degradation, the active agent is connected to the chemical scaffold by covalent bonding. In other embodiments wherein a pH sensitive release of the active agent is desired, the active agent may be connected to the chemical scaffold by ionic coupling.

Various factors, such as the mechanical strength, swelling behavior, capacity to undergo hydrolysis, and the like may affect release rates of the active agent, as is known in the art. The chemical scaffold can be engineered and specifically designed and/or selected to provide the desired biodegradation rate and release profile of the active agent for a selected duration. The rate of release may be manipulated, such as by adjusting features of the scaffold like, changing the ratio of components of the scaffold material, adjusting the level of cross-linking, level of drug loading, etc.

III. The Active Agent

In addition to the scaffold, the intraocular drug delivery systems and methods discussed herein further include an active agent.

1. Examples of Active Agents

Virtually any type of active agent may be used with the drug delivery apparatuses, systems and methods described herein. For example, possible active agents include, but are not limited to, cytokines, growth factors, proteins, peptides or peptidomimetics, bioactive agents, photosensitizing agents, radionuclides, toxins, anti-metabolites, signaling modulators, anti-cancer antibiotics, anti-cancer antibodies, angiogenesis inhibitors, radiation therapy, chemotherapeutic compounds, anti-infective agent, an anesthetic agent, an anti-VEGF agent, an anti-inflammatory agent, an intraocular pressure reducing agent, or a combination thereof.

A variety of therapeutic agents can be delivered using the drug delivery systems described herein, including: anesthetics, analgesics, cell transport/mobility impending agents such as colchicine, vincristine, cytochalasin B and related compounds; antiglaucoma drugs including beta-blockers such as timolol, betaxolol, atenolol, and prostaglandins, lipid-receptor agonists or prostaglandin analogues such as bimatoprost, travoprost, latanoprost, unoprostone etc; alpha-adrenergic agonists, brimonidine or dipivefrine, carbonic anhydrase inhibitors such as acetazolamide, methazolamide, dichlorphenamide, diamox; and neuroprotectants such as nimodipine and related compounds.

Additional examples include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; anti-fungal agents such as fluconazole, nitrofurazone, amphotericin B, ketoconazole, and related compounds; anti-viral agents such as trifluorothymidine, acyclovir, ganciclovir, DDI, AZT, foscamet, vidarabine, trifluorouridine, idoxuridine, ribavirin, protease inhibitors and anti-cytomegalovirus agents; antiallergenics such as methapyriline; chlorpheniramine, pyrilamine and prophenpyridamine; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline, and tetrahydrazoline; miotics, muscarinics and anti-cholinesterases such as pilocarpine, carbachol, di-isopropyl fluorophosphate, phospholine iodine, and demecarium bromide; mydriatics such as atropine sulfate, cyclopentolate, homatropine, scopolamine, tropicamide, eucatropine; sympathomimetics such as epinephrine and vasoconstrictors and vasodilators; Ranibizumab, Bevacizamab, and Triamcinolone.

Anti-inflammatories, such as non-steroidal anti-inflammatories (NSAIDs), may also be delivered, such as cyclooxygenase-1 (COX-1) inhibitors (e.g., acetylsalicylic acid, for example ASPIRIN from Bayer AG, Leverkusen, Germany; ibuprofen, for example ADVIL from Wyeth, Collegeville, Pa.; indomethacin; mefenamic acid), COX-2 inhibitors (CELEBREX from Pharmacia Corp., Peapack, N.J.; COX-1 inhibitors), including a prodrug NEPAFENAC; immunosuppressive agents, for example Sirolimus (RAPAMUNE, from Wyeth, Collegeville, Pa.), or matrix metalloproteinase (MMP) inhibitors (e.g., tetracycline and tetracycline derivatives) that act early within the pathways of an inflammatory response. Anticlotting agents, such as heparin, antifibrinogen, fibrinolysin, anti clotting activase, for example, may also be delivered.

Antidiabetic agents that may be delivered include acetohexamide, chlorpropamide, glipizide, glyburide, tolazamide, tolbutamide, insulin, aldose reductase inhibitors, for example. Some examples of anti-cancer agents include 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levamisole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine.

Hormones, peptides, steroids, nucleic acids, saccharides, lipids, glycolipids, glycoproteins, and other macromolecules may be delivered. Examples include: endocrine hormones such as pituitary, insulin, insulin-related growth factor, thyroid, growth hormones; heat shock proteins; immunological response modifiers such as muramyl dipeptide, cyclosporins, interferons (including á, â, and ã interferons), interleukin-2, cytokines, FK506 (an epoxy-pyrido-oxaazcyclotricosine-tetrone, also known as Tacrolimus), tumor necrosis factor, pentostatin, thymopentin, transforming factor beta2, erythropoetin; antineogenesis proteins (e.g., anti-VEGF, Interferons), among others and anticlotting agents including anticlotting activase. Further examples of macromolecules that may be delivered include monoclonal antibodies, brain nerve growth factor (BNGF), ciliary nerve growth factor (CNGF), vascular endothelial growth factor (VEGF), and monoclonal antibodies directed against such growth factors. Additional examples of immunomodulators include tumor necrosis factor inhibitors such as thalidomide.

In addition, nucleic acids may also be delivered, wherein the nucleic acid may be expressed to produce a protein that may have a variety of pharmacological, physiological or immunological activities.

By way of non-limiting example, other possible active agents include anti-coagulant, an anti-proliferative, imidazole antiproliferative agent, a quinoxaline, a phsophonyl-methoxyalkyl nucleotide analog, a potassium channel blocker, and/or a synthetic oligonucleotide, 5-[1-hydroxy-2-[2-(2-methoxyphenoxyl)ethylamino]ethyl]-2-methylbenzenesul-fonamide, a guanylate cyclase inhibitor, such as methylene blue, butylated hydroxyanisole, and/or N-methylhydroxylamine, 2-(4-methylaminobutoxy) diphenylmethane, apraclonidine, a cloprostenol analog or a fluprostenol analog, a crosslinked carboxy-containing polymer, a sugar, and water, a non-corneotoxic serine-threonine kinase inhibitor, a nonsteroidal glucocorticoid antagonist, miotics (e.g., pilocarpine, carbachol, and acetylcholinesterase inhibitors), sympathomimetics (e.g., epinephrine and dipivalylepinephxine), beta-blockers (e.g., betaxolol, levobunolol and timolol), carbonic anhydrase inhibitors (e.g., acetazolamide, methazolamide and ethoxzolamide), and prostaglandins (e.g., metabolite derivatives of arachidonic acid, or any combination thereof.

Additional examples of beneficial drugs that may be employed in the present invention, and the specific conditions to be treated or prevented thereby, are disclosed in Remington, supra; The Pharmacological Basis of Therapeutics, by Goodman and Gilman, 19th edition, published by the MacMillan Company, London; and The Merck Index, 13th Edition, 1998, published by Merck & Co., Rahway, N.J., which is incorporated herein by reference. The above list of active agents is not meant to be exhaustive. A wide variety of drugs or agents may be used in the present invention, without restriction on molecular weight or like factors.

2. Examples of Conditions and/or Diseases that May be Treated

The systems and methods disclosed herein may be used to treat a variety of diseases and/or conditions. Non-limiting examples include: age-related macular degeneration, eye infections (including, but not limited to, infections of the skin, eyelids, conjunctivae, and/or lacrimal excretory system), orbital cellulitis, dacryoadenitis, hordeolum, blepharitis, conjunctivitis, keratitis, corneal infiltrates, ulcers, endophthalmitis, panophthalmitis, viral keratitis, fungal keratitis herpes zoster ophthalmicus, viral conjunctivitis, viral retinitis, uveitis, strabismus, retinal necrosis, retinal disease, vitreoretinopathy, diabetic retinopathy, cytomegalovirus retinitis, cystoids macular edema, herpes simplex viral and adenoviral injections, scleritis, mucormycosis, canaliculitis, acanthamoeba keratitis, toxoplasmosis, giardiasis, leishmanisis, malaria, helminth infection, etc.

It should also be appreciated that medical conditions besides ocular conditions can be treated with the systems and methods described herein. For example, the systems can deliver active agents for the treatment of inflammation, infection, or cancerous growth. It should also be appreciated that any number of active agent combinations can be delivered using any of the systems and methods described herein.

IV. Implantation of the Drug Delivery System

The drug delivery system may be implanted into the eye by any manner known to one of ordinary skill in the art. For example, when a mechanical scaffold is employed, considerations must be made in size and manner of implantation for intraocular lens (IOL) replacement.

In certain exemplary embodiments, the drug delivery system may be implanted by making an incision in an exterior layer of the eye, such as the pars plana, and inserting the drug delivery system into the desired segment of the eye. An implantation via the pars plana has certain advantages, at least in that it avoid choroids and retinal blood supply when implanting the delivery system into, for example, the posterior chamber.

In certain embodiments, and as particularly illustrated in FIG. 2C and 3B, the drug delivery system may be implanted in the vitreous body 104. Placement in the vitreous body may be useful for treatment of retinal diseases. In embodiments wherein the delivery system is implanted into the vitreous body, a partial or complete vitrectomy may be performed to remove at least a portion of the vitreous humor to provide the necessary volume of space to accommodate the delivery system.

In other embodiments, and as particularly illustrated in FIGS. 3C and 3D, the drug delivery system may be implanted into the capsular bag. Placement in the capsular bag may be particularly useful for treatment or prevention of posterior capsular opacification or cataracts, by way of non-limiting example. Patients having cataracts often undergo an intraocular lens (IOL) replacement procedure, in which a surgeon performs a capsulorhexis, removes the cataract and inserts an IOL. In such situations, the delivery system of the present invention may be implanted before and/or after inserting the IOL. For example, and as particularly illustrated in FIG. 3D, an exemplary embodiment includes a generally ring shaped mechanical scaffold 112, 114 that is implanted before or after inserting the IOL 110, such that the scaffold(s) is/are positioned to be above and/or below the haptics of the IOL 110. It is to be appreciated that more than one scaffold(s) may be used within the capsular bag or in combinations with one or more scaffolds within the vitreous body, and that the scaffolds may be the same or different and may have a different active agent release profile and/or contain different active agents. For example, in an embodiment as described above, a lower scaffold 114 may deliver an anti-PCO agent over 6 months, while an upper scaffold 112 may deliver an anti-inflammatory for 2 weeks. Another particular advantage of embodiments employing a drug delivery apparatus in the capsular bag is the provision of an additional mechanical barrier to PCO growth.

In certain embodiments employing a mechanical scaffold, the mechanical scaffold may be coated with a lubricating composition to assist in the implantation of the drug delivery system. Suitable coatings may be the same or similar to coatings used to lubricate an IOL for insertion into the eye. For example, suitable lubricating coatings may be those identified in U.S. Pat. No. 8,053,078, which is incorporated herein by reference.

After implanting the delivery system into the eye, the scaffold may be positioned as desired based on the location of implantation and the desired location of release of the active agent. In certain embodiments, the dimensions of the scaffold may be adjusted after implantation into the eye. For example, the scaffold may include an adjustment extension(s), screw(s), tab(s), or the like that allows a surgeon to adjust the dimensions (or placement) of the scaffold. For example, the screw may be placed on the inner wall of the scaffold, which is configured to shrink or expand when the screw is turned.

In certain embodiments, as discussed above, the scaffold may be made from a material that is capable of being physically expanded. In such embodiments, the scaffold may be expanded by any method known to one of ordinary skill in the art. For example, the scaffold may be expanded by a balloon. In a manner similar to a stent as will be understood to the skilled artisan, the scaffold may be expanded so as to put a slight amount of pressure on the interior wall of the posterior chamber. The pressure may ensure that the scaffold remains in place and outside of the visual axis (in contrast to a stent, which is used to support the walls of an artery or vein). The exact amount of pressure exerted on an interior portion of the eye may be optimized depending on factors including, but not limited to, patient tolerance, location of implantation, etc. In certain exemplary embodiments, the pressure that the scaffold exerts on the interior wall of the respective portion of the eye may be sufficient, on its own, to completely hold the scaffold in place. In other exemplary embodiments, an adhesive, suture, or the like may be used to at least partially hold the scaffold in place. By way of example, the amount of pressure exerted on the interior wall of the eye in defining the location of a scaffold may be similar to the pressure exerted on the interior wall of the eye by an epiretinal prosthesis.

Of course, in particular exemplary embodiments, the dimensions of the scaffold may be such that the scaffold may exert the slight pressure on the interior wall of the desired portion of the eye without having to be physically expanded. For example, the scaffold may be folded prior to insertion into the eye and unfolded after insertion. The scaffold may be made from a material that is sufficiently stiff so that when the scaffold is forced in the proper position, the desired level of pressure may be exerted on the interior wall to maintain location, function, and avoid over-exertion of pressure on the eye. In such cases, and as discussed above, if the pressure exerted by the scaffold is insufficient to maintain location, an adhesive, suture, or the like may be used in conjunction with the pressure exerted to maintain location.

In other embodiments, in addition to or alternatively to the scaffold being held in place by exerting pressure on the interior wall of a segment of the eye, the scaffold may simply be attached to the interior wall of a desired segment of the eye. For example, the scaffold may be attached with an adhesive, a suture, or any other type of attachment mechanism.

In embodiments utilizing a chemical scaffold, the chemical scaffold may be implanted by injecting the scaffold into the desired intraocular segment of the eye. For example, the chemical scaffold may be used as a partial or complete replacement of the vitreous humor. In such embodiments, at least a partial vitrectomy would be performed prior to implantation of the drug delivery system.

In certain embodiments employing a chemical scaffold, the drug delivery system may be implanted into the capsular bag. For example, the drug delivery system may be implanted during a phacoemulsification and IOL implantation procedure. No vitrectomy would be required in such an instance, as will be understood to those skilled in the pertinent arts.

It will be understood that the embodiments of the present invention that are illustrated and described are merely exemplary, and that a person skilled in the art may thus make many variations and modifications thereto. Therefore, all such embodiments, variations and modifications are intended to be included within the scope of the present invention as defined by the claims set forth herein.

What is claimed is:

1. A method of providing intraocular delivery of an active agent in an eye, comprising:
   providing an implantable scaffold, wherein the scaffold comprises an interior reservoir and is formed from a flexible material, wherein the scaffold comprises a mechanical scaffold in the shape of a closed ring;
   associating the active agent with the scaffold;
   performing an intraocular implantation of the scaffold and the active agent;
   positioning an external reservoir configured to be positioned outside of the eye when the scaffold is intraocularly implanted, wherein the external reservoir is separate from the scaffold and comprises an injection port;
   fluidly connecting the external reservoir to the interior reservoir via a tube;
   delivering the active agent from the scaffold following the intraocular implantation; and
   refilling the interior reservoir with the active agent via the injection port of the external reservoir after the intraocular implantation.

2. The method of claim 1, wherein associating the active agent with the scaffold comprises filling at least a portion of the mechanical scaffold with the active agent.

3. The method of claim 2, wherein delivering the active agent includes at least release of the active agent from the filled portion of the scaffold.

4. The method of claim 1, wherein the interior reservoir contains at least a portion of the active agent.

5. The method of claim 4, wherein the interior reservoir releases at least a portion of the active agent in response to a condition within the eye.

6. The method of claim 1, wherein the scaffold comprises a coating comprising at least a portion of the active agent.

7. The method of claim 6, further comprising releasing the active agent from the coating over time.

8. The method of claim 1, wherein the active agent is delivered over a period of at least 6 months.

9. The method of claim 1, wherein the active agent is delivered over a period of at least 1 year.

10. The method of claim 1, wherein the flexible material is a polymer.

11. The method of claim 10, wherein the polymer is selected from the group consisting of a polyimide, polyvinylidene fluoride, silicone, polytetrafluoroethylene, expanded polytetrafluoroethylene, differential fluoropolymer, fluorinated ethylene propylene, polyolefins, polypropylene, poly(methyl methacrylate), acrylic polymers, polyethylene terephthalate, polyethylene, polylactide, parylene, nylon, polyether ether ketone, polysulfone, polyamideimides, polyether block amides, polyurethanes, thermoplastic elastomers, liquid crystal polymers, and combinations thereof.

12. The method of claim 1, wherein the flexible material is a metal.

13. The method of claim 12, wherein the metal is selected from the group consisting of nitinol, platinum, stainless steel, molybdenum, gold, and combinations thereof.

14. The method of claim 1, wherein the flexible material is a combination of metal and polymer.

15. The method of claim 1, wherein said scaffold further comprises a chemical scaffold comprising the active agent.

16. The method of claim 15, wherein the chemical scaffold comprises a polymeric gel.

17. The method of claim 16, wherein the polymeric gel comprises a polysaccharide.

18. The method of claim 17, wherein the polysaccharide has an average molecular weight of 700 kDa or greater.

19. The method of claim 17, wherein the polysaccharide has an average molecular weight of 1000 kDa or greater.

20. The method of claim 17, wherein at least two polysaccharides are cross-linked through carboxylic acid groups.

21. The method of claim 17, wherein at least two polysaccharides are cross-linked through hydroxyl groups.

22. The method of claim 16, wherein the active agent is released from the polymeric gel upon degradation of the polymeric gel.

23. The method of claim 15, wherein the active agent is connected to the chemical scaffold by covalent bonding.

24. The method of claim 15, wherein the active agent is ionically coupled to the chemical scaffold.

* * * * *